United States Patent [19]

Ganguly et al.

[11] 4,129,720

[45] Dec. 12, 1978

[54] AMINOEVERNINOMICIN AND DERIVATIVES THEREOF

[75] Inventors: Ashit K. Ganguly, Upper Montclair; Viyyoor M. Girijavallabhan, East Orange; Olga Sarre, Verona; Hans Reimann, Wayne, all of N.J.

[73] Assignee: Schering Corporation, Kenilworth, N.J.

[21] Appl. No.: 833,838

[22] Filed: Sep. 16, 1977

Related U.S. Application Data

[63] Continuation-in-part of Ser. No. 768,124, Feb. 14, 1977, abandoned.

[51] Int. Cl.² ............................................. C07H 17/04
[52] U.S. Cl. ...................................... 536/17; 424/180
[58] Field of Search ........................................ 536/17

[56] References Cited

U.S. PATENT DOCUMENTS

| | | | |
|---|---|---|---|
| 3,920,629 | 11/1975 | Ganguly et al. | 536/17 |
| 3,998,708 | 12/1976 | Kabasakalian et al. | 536/17 |
| 4,006,225 | 2/1977 | Ganguly et al. | 536/17 |

*Primary Examiner*—Johnnie R. Brown
*Attorney, Agent, or Firm*—Raymond A. McDonald; Carver C. Joyner

[57] ABSTRACT

Everninomicin B, C or D may be converted to amino derivatives by reductive means. The amino derivatives may, subsequently, be converted to novel N-acyl, N-alkyl or N,N-dialkyl derivatives. Alternatively, everninomicins B, C or D may be converted to N-acyl-N-hydroxylamino derivatives also by reductive means. The derivatives so-produced and the non-toxic pharmaceutically acceptable cationic salts thereof are novel and are antibacterial agents.

24 Claims, No Drawings

AMINOEVERNINOMICIN AND DERIVATIVES THEREOF

THE PRIOR ART

This application is a continuation-in-part of copending application Ser. No. 768,124, filed Feb. 14, 1977, now abandoned.

A mixture of everninomicin antibiotics including everninomicin B, everninomicin C and everninomicin D are produced when *Micromonospora carbonacea* var. *carbonacea* NRRL 2972 or a variant thereof *Micromonospora carbonacea* var. *aurantiaca* NRRL 2997 are subjected to submerged aerobic fermentation. The fermentation conditions are described in U.S. Pat. No. 3,449,078. Also described in the art are the physical characteristics and structures of everninomicins B, C and D, each of the compounds having a nitro group. U.S. Pat. No. 3,901,973 described a method for reducing said nitro groups to produce the corresponding hydroxylaminoeverninomicins using aluminum amalgam in an aprotic solvent having a high dielectric constant. When everninomicin D is reduced according to the disclosed procedure, a novel antibiotic, everninomicin 1, is also produced.

U.S. Pat. No. 3,915,956 discloses a method for reducing everninomicins B, C and D with aluminum amalgam in aqueous alkanol to yield the corresponding hydroxylaminoeverninomicin, plus the corresponding nitroso derivative. Also disclosed in the patent is a process for converting the respective hydroxylaminoeverninomicins to nitrones by reaction of said compounds with an aldehyde in an alcoholic medium under anhydrous conditions. In none of the prior art patents or publications is the formation of an aminoeverninomicin described.

We have now discovered that everninomicins B, C and D may be converted to their respective amino derivatives by catalytic hydrogenation using a conventional metal catalyst in a solvent having a high dielectric constant. A preferred procedure for effecting the reduction consists of hydrogenating a basic salt of everninomicin B, C or D (e.g. N-methylglucamine) in methoxyethanol wherein Raney nickel is employed as the catalyst.

Aminoeverninomicin B, C and D may be prepared by reducing certain hereinafter described oxazolines of hydroxylaminoeverninomicin B, C or D in a medium comprising water and a miscible organic solvent using a reducing agent consisting of zinc and ammonium chloride or zinc and tetraloweralkylammonium hydroxides. Hydroxylaminoeverninomicin B, C or D may also be converted to the corresponding amino derivative by exhaustive reduction using aluminum amalgam containing from about 5 grams to about 15 grams of aluminum per gram of hydroxylamineverninomicin B, C or D.

In its product aspect this invention relates to the amino, N-acylamino, N-acyl-N-hydroxylamino, N-alkylamino and N,N-dialkylamino derivatives of everninomicin B, C and D and their non-toxic pharmaceutically acceptable cationic salts.

The amino derivatives of the respective antibiotics may be depicted as shown in the following formulae:

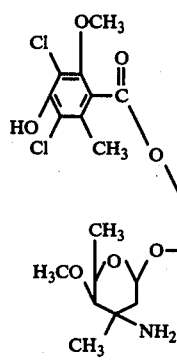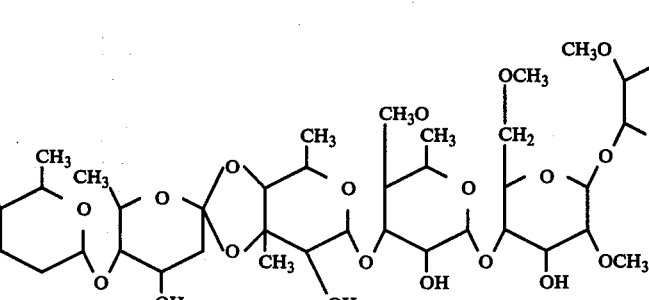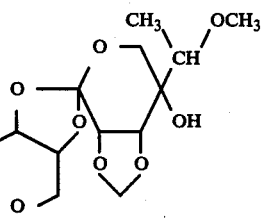

Aminoeverninomicin B

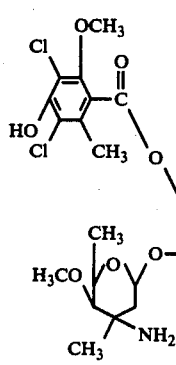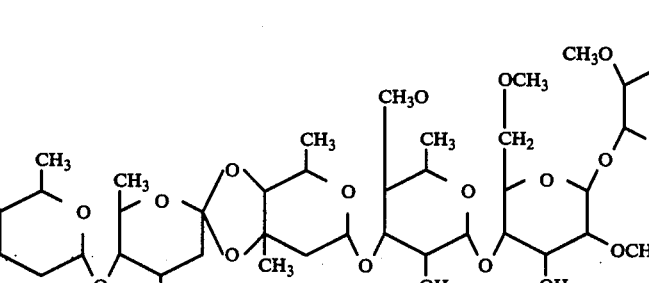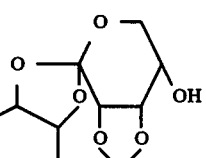

Aminoeverninomicin C

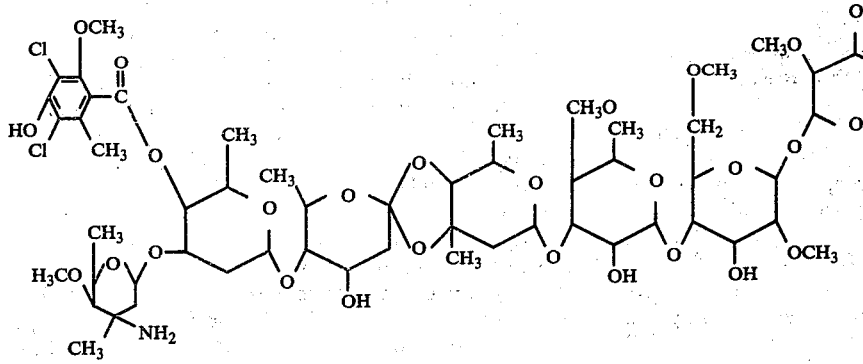

Aminoeverninomicin D

As used herein, the term acyl embraces monovalent residues derived from carboxylic acids having 1 to 12 carbon atoms. Further, the term embraces such residues derived from straight chain, branched chain and cyclized acids including aromatic acids having up to 12 carbon atoms.

The term acyl also embraces monovalent residues derived from aminoacids. Exemplary of those carboxylic acids from which the acyl group may be derived are acetic, propionic, valeric, dodecanoic, pivalic, isopropylcarboxylic, adamantanecarboxylic, cyclobutylcarboxylic, cycloheptyl carboxylic, benzoic, phenylacetic, γ-phenylbutyric, malic, lactic, mandelic, chloracetic, bromoacetic, cystine, thiolactic thioglycollic, glycine, valine, phenylglycine, threonine, tyrosine, phenylalanine, thiophene acetic, furoic, furan acetic, tetrazyl acetic acids, and the like.

The term alkyl is a member selected from the group consisting of monovalent alkane radicals having 1 to 12 carbon atoms. The term embraces such radicals derived from straight chain, branched chain and cyclized hydrocarbons and when used in conjunction with the prefix "lower", alkyl groups having 1 to 6 carbon atoms are intended. Exemplary of the alkyl radicals are methyl, ethyl, isopropyl, cyclobutyl, valeryl and capryl and the like.

In one of its process aspects, this invention relates to a method of eliciting an antibacterial response which comprises administering a therapeutically effective quantity of a compound selected from the group consisting of aminoeverninomicin B, C and D, derivatives thereof wherein the amino group bears an acyl, alkyl, or an acyl plus a hydroxy substituent and non-toxic pharmaceutically acceptable cationic salts of said compounds or of said derivatives.

In another of its process aspects, this invention relates to a process for preparing aminoeverninomicin B, aminoeverninomicin C and aminoeverninomicin D which comprises subjecting an isoxazoline derivative of a member selected from the group consisting of hydroxylaminoeverninomicin B, hydroxylaminoeverninomicin C and hydroxylaminoeverninomicin D to the reducing action of zinc and ammonium chloride, or zinc and tetraloweralkylammonium hydroxide in a medium comprising water and a miscible organic solvent.

In still another of its process aspects, this invention relates to a process for preparing aminoeverninomicin B, aminoeverninomicin C and aminoeverninomicin D which comprises hydrogenating everninomicin B, C or D, or a basic salt thereof using a conventional metal catalyst in a solvent having a high dielectric constant.

In yet another of its process aspects, this invention relates to a process for preparing aminoeverninomicin B, aminoeverninomicin C and aminoeverninomicin D which comprises chemically reducing everninomicin B, C or D using soluble chromous salts in a water miscible organic solvent.

Among the solvents suitable for the reduction processes of this invention are the following alcohols such as methanol, ethanol and isopropanol; ethers such as tetrahydrofuran, dioxane, glyme, diglyme and methoxyethanol, and other suitable solvents such as dimethylformamide, acetonitrile and dimethylsulfoxide.

In addition to ammonium chloride, the reduction with zinc may be effected in solutions of alkali metal hydroxides, such as sodium, potassium or lithium hydroxides. Alternatively, the reduction may be effected in solutions of tetraalkylammonium hydroxides such as tetramethyl, tetraethyl, tetrapropyl, tetraisopropyl, tetrabutylammonium hydroxide and the like.

The isoxazoline intermediates of hydroxylaminoeverninomicin B, C and D are prepared from α,β-unsaturated aldehydes known in the art. The aldehydes may be represented by the general formula

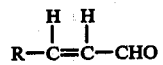

wherein R is a member of the group consisting of alkyl, cycloalkyl, aralkyl, heteroalkyl and aryl. A preferred member of the group comprising such aldehydes is cinnamaldehye. The nitrone prepared therefrom is converted to the corresponding isoxazoline in situ and may be reduced without isolation. However, isolation is preferred since it removes the intermediate from residual aldehyde thereby conserving the reducing agent by preventing it from being consumed by the residual aldehyde which is also susceptible to reduction under the reaction conditions.

The aminoeverninomicins readily react with acylating agents to yield diacyl derivatives wherein both the amino function and the phenolic hydroxyl function on the dichloroisoeverninic acid moiety are acylated. Partial hydrolysis under mild basic conditions readily removes the acyl function from the phenolic hydroxyl thereby yielding the corresponding acylaminoeverninomicin. Among the acylating agents suitable for the foregoing acylation are the conventional acyl anhydrides (e.g. acetic anhydride), mixed anhydrides (e.g. cyclohexyl carboxylic acid in admixture with a chloroformate or p.toluenesulfonyl chloride) or the like.

Alternatively, the mono-N-acyl amides may be prepared directly from the amine by acylation in the presence of alcohols, such as isopropanol, thereby avoiding the acylation of the phenolic or alcoholic hydroxyl groups.

In general, the N-acyl derivatives of the aminoeverninomicins may be purified by crystallization from ethanol, the yields being extremely high, in some cases, nearing quantitative yields.

Acylaminoeverninomicins may also be prepared from everninomicin B, everninomicin C or everninomicin D by reduction of the antiobiotics with zinc in an acid free acyl anhydride followed by hydrolysis of the O-acyl formed by acylation of the phenol. However, in this process there is also produced a substantial amount of N-hydroxy-N-acyl aminoeverninomicins which compounds are also antibacterial agents.

N-alkylaminoeverninomicins may be prepared by reductive alkylation procedures generally known in the art. In a very facile manner, an aminoeverninomicin may be reacted with an aldehyde in a suitable solvent, such as an alcohol, preferably methoxyethanol and the reaction mixture subjected to hydrogenation in the presence of a metal catalyst, preferably active Raney nickel under pressure.

Alternatively, N-alkylaminoeverninomicins may be prepared by reductive alkylation of the Schiffs bases in situ. In this procedure, the aminoeverninomicin is reacted with the appropriate aldehyde in a non-reactive solvent. The reaction product is then reacted with a suitable reducing agent (e.g. sodium cyanoborohydride) without isolation. This reaction often yields the desired product in the form of a boron complex which contains about one atom of boron per molecule of N-alkylaminoeverninomicin.

The boron complex may be treated with aluminum amalgam in aqueous alcohol to yield desired N-alkylaminoeverninomicin. N,N-dialkylaminoeverninomicins may also be prepared by reductive alkylation procedures. In a preferred process, the aminoeverninomicin is subjected to hydrogenation at atmospheric pressure, preferably in an alcoholic solution containing an excess of aldehyde. The preferred hydrogenation catalyst is platinum oxide.

The compounds of this invention have a phenolic group on the dichloroisoeverninic acid moiety which group forms non-toxic pharmaceutically acceptable cationic salts. These salts may be of the alkali or alkaline earth metal type, or alternatively, may be ammonium or substituted ammonium salts wherein the amine is selected from organic bases of which the following are exemplary; trialkylamines, procaine, dibenzylamine, N-benzylbetaphenethylamine, N,N'-dibenzylethylenediamine, dehydroabietylamine, N,N'-bisdehydroabietyl-ethylenediamine and N-(lower)-alkylpiperidines, e.g. N-ethylpiperidine and the like. Also included within the term "pharmaceutically acceptable cationic salts" are salts derived from N-methylglucamine.

The pharmaceutically acceptable cationic salts (e.g. sodium salt) are prepared according to known procedures such as by reacting an equivalent quantity of base (e.g. sodium hydroxide) with an everninomicin derivative in an aqueous solution and lyophilizing the resulting solution.

The hydroxylaminoeverninomicin B, C and D starting compounds may be prepared by the procedure set forth in U.S. Pat. No. 3,915,956, issued Oct. 28, 1976, which patent we incorpoate by reference.

Specific examples of the foregoing reactions are set forth below for the purpose of further describing the invention and are not to be construed as limiting the scope of the same.

EXAMPLE 1

Aminoeverninomicin D N-Methylglucamine Salt

Dissolve 1.0 g. of everninomicin D and 0.2 g. of N-methylglucamine in 60 ml. of methoxyethanol. Hydrogenate the mixture in the presence of 1.5 ml. of Raney nickel slurry at 30 psi for about 40 hours, at which time hydrogen uptake is substantially complete. Filter the suspension and concentrate the filtrate to obtain thereby the product of this example.

Yield - 1.1 g. m.p. 184°–186° C $[\alpha]_D^{26} = -21.2°$ (CH$_3$OH)

EXAMPLE 2

Aminoeverninomicin D

A. 3-(5-Phenyl-isoxazolin-2-yl) Everninomicin D

Dissolve 1.0 g. of hydroxylaminoeverninomicin D and 1.0 ml. of cinnamaldehyde in 10 ml. of (peroxide free) tetrahydrofuran. Heat the solution on a steam bath until the hydroxylaminoeverninomicin D has completely reacted. Complete reaction is determined by thin layer chromatography on a silica gel plate using a solvent system consisting of a 1:1 mixture of acetone and benzene, the disappearance of the spot having an Rf of 0.45 being indicative of complete reaction.

The title product is isolated by preparative thin layer chromatography using silica gel plates and the same solvent system used to monitor the reaction. The product obtained thereby has the following physical constants.

Yield - 1.0 g. m.p. 182°–184° C $[\alpha]_D^{26} = -72.4°$ (CH$_3$OH)

B. Aminoeverninomicin D

Dissolve 500 mg. of 3-(5-phenyl-isoxazolin-2-yl) everninomicin D in 25 ml. of tetrahydrofuran, and 600 mg. of zinc followed by 1.5 g. of ammonium chloride in 8.0 ml. of water. Stir the suspension until the reduction is complete, filter and concentrate to a residue obtaining thereby the product of this example.

Yield - 335 mg. m.p. 184°–186° C $[\alpha]_D^{26} = -21.2°$ (CH$_3$OH)

In a similar manner, by subjecting an equivalent quantity of hydroxylaminoeverninomicin B or hydroxylaminoeverninomicin C to the process of this example, the corresponding amino derivatives may be prepared.

EXAMPLE 3

Aminoeverninomicin D

Prepare a suspension of 5.0 g. of aluminum powder in 20 ml. of distilled water. Add a solution containing 80 mg. of mercuric chloride in 10 ml. of water while stirring. Add a solution containing 2 g. of everninomicin D in 100 ml. of ethanol after gas evolution of the aluminum amalgam commences. Monitor the reaction by thin layer chromatography on silica gel using a solvent system consisting of methanol:chloroform, 20:80 v/v. When the product consists of a mixture of hydroxylamino and aminoeverninomicin D, filter the reaction mixture, wash the solids with ethanol and combine the filtrate and washes. Prepare a fresh batch of aluminum amalgam (from 25 g. of aluminum) and repeat the reduction process by adding the combined filtrate and washes to the reducing agent. Monitor the reaction by thin layer chromatography using the above described solvent system.

Yield - 1.5 g. m.p. 184°-186° C $[\alpha]_D^{26} = -21.2°$ (CH$_3$OH)

In a similar manner, by subjecting an equivalent quantity of everninomicin B or everninomicin C to the process of this example, the corresponding amino derivative may be prepared.

EXAMPLE 4

Aminoeverninomicin D

Dissolve 1.0 g. of everninomicin D in 30 ml. of oxygen free methanol, add 1.5 g. of chromous acetate with stirring and continue stirring for about 3 hours. Remove the methanol by distillation in vacuo, dissolve the residue in 25 ml. of an aqueous solution containing 1.0 g. of N-methylglucamine. Add to the resulting solution 20 ml. of a 5% sodium carbonate solution. Centrifuge the resulting mixture, decant the supernatant leaving behind the precipitated chromium salts. Acidify the supernatant to pH 5.0 using phosphate buffer to obtain aminoeverninomicin in admixture with some hydroxylaminoeverninomicin and nitrosoeverninomicin which compounds may be separated by chromatography on silica gel using a solvent system consisting of methanol:chloroform 20:80 v/v.

Yield - 450 mg. m.p. 184°-186° C $[\alpha]_D^{26} = -21.2°$ (CH$_3$OH)

In a similar manner, by subjecting an equivalent quantity of everninomicin B or everninomicin C to the process of this example, the corresponding amino derivatives may be prepared.

EXAMPLE 5

N-Acetylaminoeverninomicin D

Dissolve 500 mg. of aminoeverninomicin D in 4 ml. of acetic ahydride with stirring. Add 600 mg. of calcium carbonate and continue stirring. Monitor the reaction by thin layer chromatography on silica gel using acetone-benzene 40:60 v/v as the solvent system. The reaction is permitted to continue until the amine has completely reacted, then the excess acetic anydride is removed under high vacuum. Add 20 ml. of N sodium bicarbonate to destroy the residual acetic anhydride. Dissolve the diacyl product in 10 ml. of methanol and 10 ml. of a 20% solution of tetraethylammonium hydroxide. Monitor the hydrolysis reaction by thin layer chromatography using the same system described above. When the phenolic acyl function is removed, adjust the reaction mixture to pH 6.5 with phosphate buffer followed by extraction of the product with ethyl acetate. Concentrate the ethyl acetate to a residue. Crystallize the residue from ethanol to obtain thereby the product of this example.

Yield — 490 mg. m.p. 189°-191° C $[\alpha]_D^{26} = -34.7°$. (CH$_3$OH)

In a similar manner, by subjecting an equivalent quantity of aminoeverninomicin B or aminoeverninomicin C to the process of this example, the corresponding N-acetyl derivatives may be produced.

EXAMPLE 6

N-Cyclohexylcarbonylaminoeverninomicin D

Dissolve 1.3 g. of cyclohexane carboxylic acid and 1.05 g. of triethylamine in 20 ml. of anhydrous tetrahydrofuran. Cool the reaction mixture to about 5°-10° C and add 1.1 g. of ethylchloroformate with agitation. Continue agitating the reaction mixture for an additional ten minutes and filter. Add to the clear filtrate, 600 mg. of aminoeverninomicin and continue agitating the reaction mixture. Monitor the reaction by the procedure described in Example 5. When the reaction is complete, treat the reaction mixture with a solution of sodium bicarbonate and extract with ethyl acetate. Concentrate the solution containing the diacyl product to a residue, dissolve the residue in methanol and hydrolyze using a 20% solution of tetraethylammonium hydroxide in methanol to obtain thereby the product of this example.

Yield — 585 mg. m.p. 184°-186° C $[\alpha]_D^{26} = -35.9°$ (CH$_3$OH)

In a similar manner, by subjecting an equivalent quantity of aminoeverninomicin B or of aminoeverninomicin C to the procedure of this example, the corresponding N-cyclohexacylcarbonyl derivatives may be produced.

The foregoing example is directed to a general process and may be utilized to prepare N-acylaminoeverninomicin B, N-acylaminoeverninomicin C or N-acylaminoeverninomicin D derivatives of substantially any carboxylic acid of which the following are exemplary: acetic, propionic, valeric, dodecanoic, pivalic, isopropylcarboxylic, adamantanecarboxylic, cyclobutyl carboxylic, cycloheptyl carboxylic, benzoic, phenylacetic, γ-phenylbutyric acids and the like.

EXAMPLE 7

N-phenylglycylaminoeverninomicin D

Prepare a solution of 950 mg. of N-carbobenzyloxy phenylglycine in 30 ml. of anhydrous methylene chloride and add 330 mg. of triethylamine followed by 400 mg. of ethylchloroformate while stirring at −20° C. Stir for ¼ hour, add 500 mg. of aminoeverinomicin D and raise the temperature to 25° C. Monitor the reaction by the procedure described in Example 5 until the reaction is complete. Add 75 ml. of ethyl acetate, wash the resulting solution with 10 ml. of pH 6.0 phosphate buffer, then wash with 20 ml. of 1.0 N sodium bicarbonate solution and concentrate the ethyl acetate solution to residue. Dissolve the residue in 25 ml. of ethanol and hydrogenate at 30 psi in the presence of 100 mg. of palladium for about 20 hours. Remove the catalyst by filtration, basify the filtrate with 10 ml. of 20% tetraethylamminium hydroxide. Concentrate the filtrate to a residue to obtain thereby 270 mg. of the product of this example.

In a similar manner, subjecting an equivalent quantity of aminoeverninomicin B or of aminoeverninomicin C to the procedure of this example, the corresponding N-phenylglycyl derivatives may be produced.

In like manner, by replacing N-carbobenzyloxyphenylglycine with an equivalent quantity of other aminoacids bearing reductively removable amino protecting groups and by following the procedure of this example, the corresponding aminoacylamino derivatives of everninomicin B, C or D may be produced.

EXAMPLE 8

N-Acetylaminoeverninomicin D

Dissolve 500 mg. of everninomicin D in 10 ml. of acidfree acetic anhydride and add, portionwise, 800 mg. of active zinc dust. Monitor the reaction by thin layer chromatography on silica gel plates using a solvent system consisting of 40% acetone-60% benzene. When the reaction is complete, as determined by the absence of starting material, filter the reaction mixture. Concentrate the filtrate in vacuo to a residue. Basify the residue with 5 ml. of a solution consisting of 10% tetraethylammonium hydroxide in 20 ml. of methanol. Monitor the reaction by the above described thin layer system to determine when hydrolysis of the acetylated phenol is complete. Acidify the solution with pH 4.5 phosphate buffer and extract the product with ethyl acetate. Dry the extract over anhydrous sodium sulfate, concentrate the dried extract to a residue and obtain thereby 390 mg. of a solid consisting of the product of this example in admixture with N-hydroxy-N-acetyl-aminoeverninomicin D (N-acetylhydroxylaminoeverninomicin D) the latter compound having the following physical constants:

m.p. 176°-178° C $[\alpha]_D^{26} = -34°$ (CH$_3$OH) U.V. λ max. 215, 295 ($\epsilon$, 6400)

In a similar manner, by subjecting an equivalent quantity of everninomicin C to the process of this example, the corresponding N-acyl amino and the corresponding N-hydroxy-N-acyl amino derivatives may be prepared.

Likewise by substituting an equivalent quantity of other carboxylic acid anhydrides, such as propionic anhydride, n-butyric anhydride, n-valeric anhydride or the like, for acetic anydride and by repeating the process of this example, the corresponding N-acyl amino and the corresponding N-hydroxy-N-acylamino derivatives may be prepared.

EXAMPLE 9

N-Ethylaminoeverninomicin D

Dissolve 1 g. of aminoeverninomicin D in 75 ml. of methoxyethanol and 10 ml. of acetaldehyde. Hydrogenate the reaction mixture in the presence of 3.5 ml. of a slurry of activated Raney nickel catalyst at a pressure of about 30 psi for about 30 hours. Filter the reaction mixture and remove the solvent under reduced pressure to a residue. Crytallize the residue from acetone to obtain thereby the product of this example.

Yield — 950 mg. m.p. 184°-186° C $[\alpha]_D^{26} = -18°$ (CH$_3$OH) λ methanol$_{max.}$ 215 ($\epsilon$,20650), 295 ($\epsilon$, 11475)

In a similar manner, by subjecting an equivalent quantity of aminoeverinomicin B or of aminoeverninomicin C to the process of this example, the corresponding N-ethyl derivatives may be prepared.

Likewise, by substituting an equivalent quantity of other aldehydes such as propanal, n-butyraldehyde, isobutyraldehyde, n-valeraldehyde, isovaleraldehyde, n-caproaldehyde or the like for acetaldehyde and by repeating the process of this example, the corresponding N-alkylaminoeverninomicin D may be prepared.

EXAMPLE 10

N,N-Diethylaminoeverninomicin

Dissolve 500 mg. of aminoeverninomicin D in 15 ml. of ethyl alcohol and 3 ml. of acetaldehyde. Hydrogenate the reaction mixture at atmospheric pressure for about 30 hours in the presence of 200 mg. of platinum oxide catalyst. Filter the reaction mixture. Concentrate the filtrate until crystallization occurs, cool the crystalline slurry, filter and dry to constant weight.

Yield — 350 mg. m.p. 173°-175° C $[\alpha]_D^{26} = -21.4°$ (CH$_3$OH)

λmethanol$_{max.}$ 215, ($\epsilon$, 22040) 295 ($\epsilon$, 13680)

In a similar manner, by subjecting an equivalent quantity of aminoeverninomicin B or of aminoeverninomicin C to the process of this example, the corresponding N,N-diethyl derivatives may be prepared.

Likewise, by substituting an equivalent quantity of other aldehydes, such as those set forth in Example 9, for acetaldehyde and by repeating the process of this example, the corresponding N,N-dialkylaminoeverninomicin may be prepared.

EXAMPLE 11

Preparation of Basic Salts of N-acylamino Everninomicins B, C and D

A. N-Methylglucamine Salts

Suspend 1.55 g. of N-acetylaminoeverninomicin D (prepared as described above) in 25 ml. of distilled water. Add, to the suspension with agitation, .39 g. of N-methylglucamine in 20 ml. of distilled water. Agitate the suspension at 25° C until the amide is completely dissolved, then provide a nitrogen atomsphere and filter. Lyophilize the filtrate to obtain thereby the N-methylglucamine salt of N-acetylaminoeverninomicin D.

B. Sodium Salt

Suspend 1.55 g. of N-acetylaminoeverninomicin D in 15 ml. of distilled water containing 10 ml. of methanol. Add a solution of 40 mg. of sodium hydroxide in 5 ml. of distilled water with stirring. Agitate the suspension until the amide is completely dissolved then provide a nitrogen atmosphere and filter. Remove the methanol under high vacuum at room temperature then lyophilize the aqueous solution to obtain thereby the sodium salt of N-acetylaminoeverninomicin D.

In a like manner, by subjecting an equivalent quantity of N-acetylaminoeverninomicin B or N-acetylaminoeverninomicin C to the salt formations set forth above, the corresponding pharmaceutically acceptable cationic salts may be prepared.

Similarly, by subjecting an equivalent quantity of other N-acylamino or N-hydroxy-N-acylaminoeverninomicins B, C or D to the above described processes, cationic salts thereof may be produced.

Pharmaceutically acceptable cationic salts of N-alkylamino and N,N-dialkylaminoeverninomicins B, C and D may also be prepared by the procedures set forth above.

The compounds of this invention are potent antibacterial agents and are especially useful against gram-positive bacteria. They may be used to treat warm blooded animals having infections caused by susceptible bacterial species. Treatment is preferably effected by intramuscular or intravenous injection of dosage units of preparations containing the antibacterial agent in admixture with compatible pharmaceutically acceptable excipients generally used in the art. Exemplary of such preparations are those described in U.S. Pat. No. 3,915,956 issued Oct. 28, 1975 and 4,006,225 issued Feb. 1, 1977.

The compounds of this invention are preferably administered parenterally and in the form of non-toxic pharmaceutically acceptable cationic salts which are usually white and water soluble. The dosage is dependent upon various factors such as animal species being treated, infecting organism, the stage and severity of the infection and the like. Generally, the dosage administered is from about 2.5 mpk (miligram per kilogram) to about 50 mpk per day in divided dosages, the specified dosage being left to the discretion of the practitioner.

The compounds of this invention may also be used in combination with soaps and detergents to rid laboratory equipment such as glassware instruments, animal cages or the like of susceptible bacterial species.

As is generally the case in inventions such as this, certain sub-genera and certain species therein are preferred for one reason or another. The preferred compounds of this invention are N-acylaminoeverninomicin B, C and D. Especially preferred are the N-methylglucamine salts. A particularly valuable species of this invention is N-acetylaminoeverninomicin D in the form of a cationic, preferably the N-methylglucamine salt.

We claim:

1. A compound selected from the group consisting of aminoverninomicin B, aminoeverninomicin C, aminoeverninomicin D, the N-acyl, N-acyl-N-hydroxyl, N-alky, N,N-dialkyl derivatives and non-toxic pharmaceutically acceptable cationic salts thereof wherein said acyl group is derived from a carboxylic acid having 1 to 12 carbon atoms and said alkyl group is a member selected from the group having 1 to 12 carbon atoms.

2. A compound of claim 1 selected from the group consisting of aminoeverninomicin B, aminoeverninomicin C, aminoeverninomicin D, and non-toxic pharmaceutically acceptable cationic salts thereof.

3. A compound of claim 1 selected from the group consisting of N-acylaminoeverninomicin B, N-acylaminoeverninomicin C, N-acylaminoeverninomicin D and non-toxic pharmaceutically acceptable cationic salts thereof wherein the acyl group is derived from a carboxylic acid having 1 to 12 carbon atoms.

4. A compound of claim 1 selected from the group consisting of N-acyl-N-hydroxylaminoeverninomicin B, N-acyl-N-hydroxylaminoeverninomicin C, N-acyl-N-hydroxylaminoeverninomicin D and non-toxic pharmaceutically acceptable cationic salts thereof wherein the acyl group is derived from a carboxylic acid having 1 to 12 carbon atoms.

5. A compound of claim 1 selected from the group consisting of N-alkylaminoeverninomicin B, N-alkylaminoeverninomicin C and N-alkylaminoeverninomicin D and non-toxic pharmaceutically acceptable cationic salts thereof wherein the alkyl group is a member selected from the group having 1 to 12 carbon atoms.

6. A compound of claim 1 selected from the group consisting of N,N-dialkylaminoeverninomicin B, N,N-dialkylaminoeverninomicin C and N,N-dialkylaminoeverninomicin D and pharmaceutically acceptable cationic salts thereof wherein each of said alkyl groups are members selected from the group having 1 to 12 carbon atoms.

7. A compound of claim 2, said compound being aminoeverninomicin B.

8. A compound of claim 2, said compound being aminoeverninomicin C.

9. A compound of claim 2, said compound being aminoeverninomicin D.

10. A compound of claim 3, said compound being N-acetylaminoeverninomicin B.

11. A compound of claim 3, said compound being N-acetylaminoeverninomicin C.

12. A compound of claim 3, said compound being N-acetylaminoeverninomicin D.

13. A compound of claim 4, said compound being N-acetyl-N-hydroxylaminoeverniomicin B.

14. A compound of claim 4, said compound being N-acetyl-N-hydroxylaminoeverninomicin C.

15. A compound of claim 4, said compound being N-acetyl-N-hydroxylaminoeverninomicin D.

16. A compound of claim 5, said compound being N-ethylaminoeverninomicin B.

17. A compound of claim 5, said compound being N-ethylaminoeverninomicin C.

18. A compound of claim 5, said compound being N-ethylaminoeverninomicin D.

19. A compound of claim 6, said compound being N,N-diethylaminoeverninomicin B.

20. A compound of claim 6, said compound being N,N-diethylaminoeverninomicin C.

21. A compound of claim 6, said compound being N,N-diethylaminoeverninomicin D.

22. A non-toxic pharmaceutically acceptable cationic salt of the compound of claim 12.

23. A compound of claim 22, said compound being N-acetylaminoeverninomicin D sodium salt.

24. A compound of claim 22, said compound being N-acetylaminoeverninomicin D N-methylglucamine salt.

* * * * *